US009139508B2

(12) United States Patent
Pennemann et al.

(10) Patent No.: US 9,139,508 B2
(45) Date of Patent: Sep. 22, 2015

(54) METHOD AND SYSTEM FOR PRODUCING NITROBENZENE

(71) Applicant: Bayer Intellectual Property GmbH, Monheim (DE)

(72) Inventors: Bernd Pennemann, Bergisch Gladbach (DE); Juergen Munnig, Kaarst (DE); Wulf Dietrich, Cologne (DE); Andreas Karl Rausch, Kaarst (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/374,665

(22) PCT Filed: Jan. 28, 2013

(86) PCT No.: PCT/EP2013/051561
§ 371 (c)(1),
(2) Date: Jul. 25, 2014

(87) PCT Pub. No.: WO2013/113651
PCT Pub. Date: Aug. 8, 2013

(65) Prior Publication Data

US 2014/0357905 A1 Dec. 4, 2014

(30) Foreign Application Priority Data

Jan. 31, 2012 (EP) .................................... 12153202

(51) Int. Cl.

| | |
|---|---|
| ***C07C 201/08*** | (2006.01) |
| ***C07C 205/06*** | (2006.01) |
| ***C01B 17/94*** | (2006.01) |
| ***C01B 17/88*** | (2006.01) |

(52) U.S. Cl.
CPC ............... *C07C 201/08* (2013.01); *C01B 17/88* (2013.01); *C01B 17/94* (2013.01); *C07C 205/06* (2013.01)

(58) Field of Classification Search
None
See application file for complete search history.

(56) References Cited

U.S. PATENT DOCUMENTS

| | | | |
|---|---|---|---|
| 2,256,999 | A | 9/1941 | Castner |
| 4,091,042 | A | 5/1978 | Alexanderson et al. |
| 4,772,757 | A | 9/1988 | Lailach et al. |
| 5,313,009 | A | 5/1994 | Guenkel et al. |
| 5,763,697 | A | 6/1998 | Hermann et al. |

FOREIGN PATENT DOCUMENTS

| | | | |
|---|---|---|---|
| DE | 19636191 | A1 | 2/1998 |
| DE | 102009005324 | A1 | 7/2010 |
| EP | 0615951 | A1 | 9/1994 |

OTHER PUBLICATIONS

Ullmann, “Sulfuric Acid and Sulfur Trioxide”, 2005, Wiley VCH, pp. 51-52.

*Primary Examiner* — Brian J Davis
(74) *Attorney, Agent, or Firm* — Donald R. Palladino

(57) ABSTRACT

The present invention relates to a process and a plant for the production, in particular the continuous production, of nitrobenzene by means of adiabatic nitration of benzene with nitric acid in the presence of sulfuric acid, in which, following the nitration, a multi-stage concentration of the sulfuric acid is carried out by means of heating at a pressure that is reduced as compared with ambient pressure, and wherein the heating takes place using the heat generated in the adiabatic nitration of benzene.

7 Claims, 1 Drawing Sheet

METHOD AND SYSTEM FOR PRODUCING NITROBENZENE

FIELD

The present invention relates to a process and a plant for the production, in particular the continuous production, of nitrobenzene by means of adiabatic nitration of benzene with nitric acid in the presence of sulfuric acid, in which, following the nitration, a multi-stage concentration of the sulfuric acid is carried out by means of heating at a pressure that is reduced as compared with ambient pressure, and wherein the heating takes place using the heat generated in the adiabatic nitration of benzene.

BACKGROUND

Processes for the production of nitrobenzene by adiabatic nitration of benzene by means of nitric acid in the presence of sulfuric acid have already been known for some time.

Such a process was filed in its basic form, for example, as early as 1939 and granted as a patent in 1941 as U.S. Pat. No. 2,256,999.

Current, basic forms are described, for example, in U.S. Pat. No. 4,091,042, U.S. Pat. No. 5,313,009 and U.S. Pat. No. 5,763,697.

A common feature of the substantially adiabatic processes described therein is that the actual starting materials of the nitration—benzene and nitric acid—are reacted in the presence of large excesses of sulfuric acid.

Furthermore, in all the above-mentioned processes of the prior art, the nitric acid is premixed with the excess of sulfuric acid. A mixture so obtained, comprising substantially sulfuric acid and nitric acid, is referred to therein, as well as within the context of the present invention, as mixed acid.

The reaction of benzene with nitric acid to give nitrobenzene and water is highly exothermic ($\Delta H = -117$ kJ/mol), and in the processes mentioned above the large excess of sulfuric acid takes up almost quantitatively the reaction enthalpy in the form of heat liberated during the reaction, as well the water formed thereby.

It is likewise a common feature of the above-mentioned processes that at least part of the heat from the reaction enthalpy stored in the reaction product is used to re-concentrate the sulfuric acid, which becomes highly diluted with water in the course of the reaction, by evaporation of the water.

Accordingly, in U.S. Pat. No. 4,091,042, the process is carried out in four series-connected stirred vessels, the reaction product leaving the fourth stirred vessel being passed into a phase separator, which is likewise operated continuously, in which the so-called spent acid, which is substantially aqueous, is separated from the so-called crude nitrobenzene, which is substantially organic.

In connection with the present invention, spent acid denotes a substantially polar, aqueous mixture comprising water and sulfuric acid, in which portions of nitrobenzene may still be dissolved in the sulfuric acid, and crude nitrobenzene denotes a substantially non-polar, organic mixture comprising benzene and nitrobenzene, in which portions of sulfuric acid and water may still be dissolved in the nitrobenzene.

In U.S. Pat. No. 4,091,042, the spent acid is concentrated in a flash evaporator using the heat of reaction stored in the spent acid. According to U.S. Pat. No. 4,091,042, this concentration takes place at 90° C. and about 80 mbar.

According to U.S. Pat. No. 4,091,042, the crude nitrobenzene is also worked up further by being passed continuously into a four-stage counter-current extraction washer, in which acidic constituents such as sulfuric acid residues and secondary reaction products, such as, for example, dinitrophenol and picric acid, are extracted by contact with a sodium carbonate solution.

The crude nitrobenzene thus purified is finally subjected to steam distillation, in which the remaining benzene is separated off in order to be returned to the nitration.

U.S. Pat. No. 4,091,042 accordingly does not disclose a multi-stage evaporation.

In the process described in U.S. Pat. No. 5,313,009 for the adiabatic production of nitrobenzene, nitric acid is also mixed with a large amount of sulfuric acid to form the mixed acid, and benzene is metered into the mixed acid, the benzene then reacting with the nitric acid to give water and substantially nitrobenzene.

According to the process of U.S. Pat. No. 5,313,009, the temperature of the reaction, the concentration of benzene, the concentration of nitric acid and the concentration of sulfuric acid are so chosen that—in contrast to the process according to the above-mentioned U.S. Pat. No. 4,091,042—a substantially nitric-acid-free mixture of benzene, nitrobenzene, sulfuric acid and water is already obtained after a first reaction zone. That is to say, according to U.S. Pat. No. 5,313,009, the process is so operated that the conversion of nitric acid is quantitative. To that end, benzene, is used in at least stoichiometric amounts, based on the amount of citric acid.

The substantially nitric-acid-free reaction mixture obtained downstream of the reaction zone is also fed in U.S. Pat. No. 5,313,009 to a single phase separator, in which the crude nitrobenzene is separated from the spent acid.

The spent acid is fed, analogously to the process of U.S. Pat. No. 4,091,042, to a flash evaporator, in which the water is evaporated from the spent acid likewise at reduced pressure compared with ambient pressure and at elevated temperature. Here too, at least part of the heat from the reaction products is used for the concentration of the sulfuric acid in said flash evaporator.

U.S. Pat. No. 5,313,009 merely describes that the concentrated acid obtained from the flash evaporation approximately identical in terms of its composition to that used at the beginning, of the process. U.S. Pat. No. 5,313,009 does not disclose the exact pressure of the flash evaporation or the exact temperature of the flash evaporation.

Accordingly, U.S. Pat. No. 5,313,009 likewise does not disclose a multi-stage flash evaporation of the spent acid.

In the process according to U.S. Pat. No. 5,763,697 too, mention is made only of a "purification and concentration stage", but it is not disclosed in U.S. Pat. No. 5,763,697 precisely how that purification and concentration is carried out. For the rest, the process of U.S. Pat. No. 5,763,697 is similar to that of the above-described U.S. Pat. No. 5,313,009.

The above, generally known processes of the prior art are, therefore, all characterised in that the further treatment of the spent acid takes place in a single stage in a flash evaporation under reduced pressure, at least part of the heat of which comes from the adiabatic reaction of benzene with the nitric acid.

As a result, in addition to the desired evaporation of the water in order to concentrate the sulfuric acid, further constituents of the spent acid are generally evaporated at the same time, because the desired rate of separation of the water must be achieved in one stage, which, with the available heat provided by the reaction enthalpy, can be achieved only by the pronounced and in particular rapid pressure reduction.

Accordingly, in addition to the evaporation of water, there also occurs, for example, the outgassing of nitric oxides, which form as products of secondary reactions, such as, for example, oxidations, during the nitration reaction. Nitrogen monoxide and dinitrogen monoxide have boiling points of about −150° C. and −90° C., respectively, so that they cannot be recovered in the further process by condensation.

In addition to these there also form, as a result of the single flash evaporation, further products, referred to in the following as non-condensable gases, which, on account of their low boiling point, cannot be recovered economically. These result in disadvantages in particular in relation to the dimensioning of the condensation devices and devices for generating the required low pressure. In both cases, because of the significantly increased volume flows, it is necessary to use devices with larger dimensions, which, if nothing else, adversely affect the profitability of such processes.

DE 19636191 addresses the above-mentioned problems with a view to particular individual problems relating to environmental pollution. Unlike the above-mentioned prior art, it describes a multi-stage purification process for the spent acid. The multi-stage process according to DE 19636191 comprises a first step in which so-called steam-volatile organic compounds are removed by the passage of steam ("steam stripping") countercurrently at a pressure in the range of from 200 mbar to 1000 mbar, following which, in a second step, at the same pressure, a first evaporation of the water from the remaining sulfuric acid is carried out and, in a third step, the evaporation of the water is continued repeatedly at further reduced pressure.

In contrast to the processes from the preceding prior art, the heat for the evaporation of the water is supplied from outside and from a different source. The use of the heat from the nitration for the evaporation of the water from the spent acid is not disclosed.

EP 0415951 also describes a multi-stage evaporation of the water from the spent acid, which, analogously to DE 19636191, is preceded by an additional purification step in the form of steam stripping. Like DE 19636191, EP 0615951 does not disclose the use of the heat from the adiabatic nitration.

The approach described in EP 0615951 and DE 19636191 is also to be found summarised in Ullmann ("Sulfuric acid and sulfur trioxide", 2005, Wiley VCH, p. 51 to 52). Here, it is described that a multi-stage concentration of sulfuric acid according to Lurgi, (FIG. 42), in which the pressure falls from 1 bar to 70 mbar in order to produce a temperature gradient, allows an energy saving to be made. In the variants presented therein, the heat of condensation from the recondensation of the vapour of one evaporation stage is in each case used to heat the preceding stage.

However, a multi-stage concentration of sulfuric acid by evaporation as described in DE 19636191, EP 0615951 and Ullmann (2005) is expedient from the point of view of energy only if the concentration difference of the spent acid between the various stages of the concentration is sufficiently great, so that the heat of condensation from the recondensation of the vapour of the preceding evaporation stage ("vapours") can be used to heat the following stage.

In the case of the concentration of the spent acid from the nitration of benzene, that is generally not the case.

The technical teachings of DE 19636191 and EP 0615951 relate in particular to the treatment of spent acids from the nitration of toluenes, which are then to be separated from the spent acids. Unlike the nitrated benzenes of the present invention, such mono- and/or di-nitrotoluenes do not have suitable saturation temperatures, or suitable concentration differences at the saturation temperatures, so that it is not possible to apply the technical teachings contained therein to the problem of the production of nitrobenzene and the problem contained therein of separating and concentrating the sulfuric acid containing those impurities.

Accordingly, the object continues to be to provide a process which permits the production of nitrobenzene by nitration of benzene with nitric acid in the presence of sulfuric acid and which does not have the mentioned disadvantages of the prior art in relation to the production of nitrobenzene.

In particular, the process is not to have the disadvantages associated with the formation of considerable amounts of non-condensable gases dissolved in the acid—the substantially increased energy outlays for the dissipation thereof in the case of single-stage treatment—and therefore allow the devices for generating low pressure to be of smaller dimensions and accordingly less expensive.

A further problem which occurs in the prior art and has not hitherto been solved is that, owing to the very low pressures in the flash evaporators of the prior art, the saturation temperature of the vapour stream produced (vapours) is frequently close to the supply temperature of the cooling medium of conventional cooling systems (water), so that large heat exchanger surfaces are required for the condensation of that stream. Because the process pressure is close to the saturation temperature of the water, a considerable portion of the gas stream consists of steam, as a result of which the capacity requirements of the vacuum pump increase still further.

Overall, therefore, the problem according to the prior art is to provide a process for the production of nitrobenzene by nitration of benzene with nitric acid in the presence of sulfuric acid which allows the investment costs of the plant for carrying out the process to be reduced significantly.

SUMMARY

It has been found, surprisingly, that the above-mentioned object can be achieved by a process for the production of nitrobenzene by means of adiabatic nitration of benzene with nitric acid in the presence of sulfuric acid, in which a) the product mixture obtained in the nitration is separated into spent acid and crude nitrobenzene and b) at least the water contained in the spent acid is partially separated from the sulfuric acid contained therein and c) the sulfuric acid so concentrated is fed to the nitration again, which process is characterised in that i) the separation according to step b) is carried out by evaporation in two stages with an absolute pressure that falls from the first stage to the second stage from 100 mbar to 300 mbar to 50 mbar to 150 mbar, ii) the heat used for the evaporation according to step i) comes substantially from the reaction enthalpy of the nitration and iii) the product mixture obtained in the nitration has a temperature of at least 110° C.

DETAILED DESCRIPTION

Figure 1:
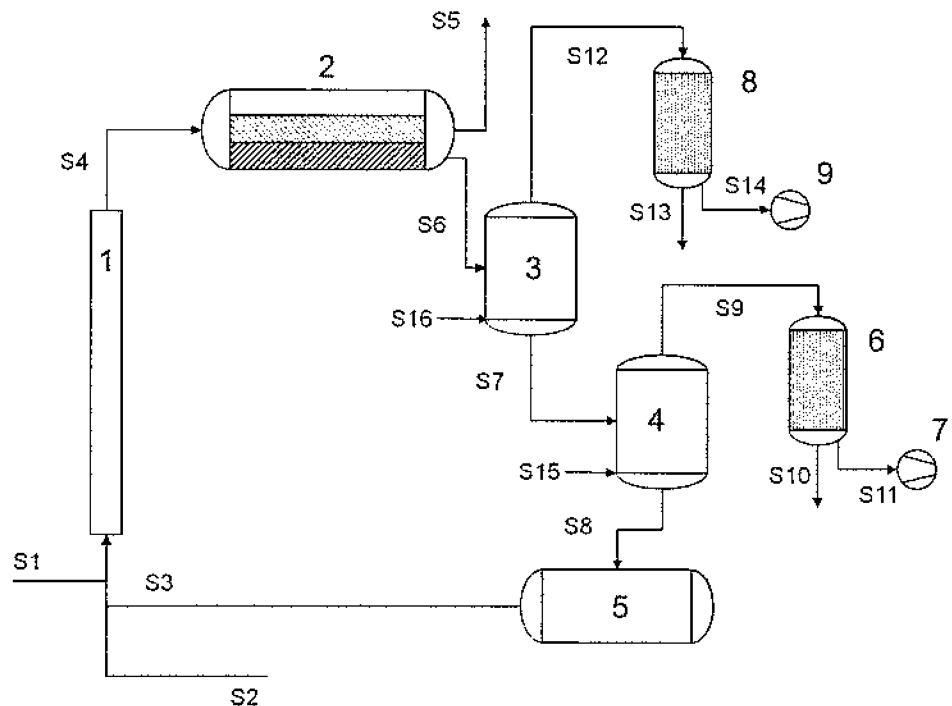
FIG. 1 shows in diagrammatic form a preferred embodiment of the process according to the invention, or of the plant according to the invention, in which a sulfuric acid stream (S3) and nitric acid (S2) and benzene (S1) are fed to a reactor (1)

In the first stage of step i) of the process according to the invention, therefore, the evaporation of water present in the sulfuric acid takes place at an absolute pressure of from 100 mbar to 300 mbar. In the second stage of step i) of the process according to the invention, the evaporation of water present in the sulfuric acid takes place at an absolute pressure of from 50 mbar to 150 mbar, the pressure naturally always being lower in the second stage than in the first stage.

The separation according to the invention by evaporation at the above-mentioned pressures according to the invention results in a number of advantages, in particular when the heat from the reaction enthalpy of the nitration is used.

Accordingly, in the first stage, separation is carried out by evaporation at a comparatively slightly reduced pressure, as a result of which the problem of the outgassing of the non-condensable gases occurs only here and the required capacity and nominal power of the device for pressure reduction (vacuum system) are consequently reduced overall.

The energy demand is lower in the first stage in particular because it is possible to work at comparatively higher pressures (i.e. pressures that are reduced to a lesser extent), while in the second stage the pressure is reduced to the extent ultimately required, the volume flow of the gases being reduced here on account of the preceding separation of the non-condensable gases, so that the energy demand is reduced here too. The interaction of the two stages, owing to the fact that the pressure is higher in the first stage and owing to the fact that the volume stream is lower in the second stage, results overall in a significantly reduced energy demand of the process as a whole, which goes beyond the sum of the energy saved in the ease of an individual measure (raised pressure in the separation only, or reduced volume stream only). It has been shown that this process is advantageous when the pressure in the first stage is at least 10 mbar, preferably 30 mbar, higher than in the second stage.

The above-mentioned separation at a comparatively high pressure additionally as the result that the above-mentioned condenser can be of smaller dimensions or, alternatively, that smaller amounts of cooling water are used, because the non-condensable gases do not have to be cooled at the same time. In addition, owing to the higher pressure in the first stage, the saturation temperature of the vapour stream that is produced increases significantly, so that condensation can be carried out with cooling-tower water even in warm climate zones and, compared to condensation against cold water, a significant improvement in the energy efficiency is achieved. Suitable condensers are all types known to the person skilled in the art. Accordingly, the condensation can take place directly or indirectly, both in a single stage and in several stages. There are suitable, for example, tube and shell heat exchangers, optionally with aftercoolers.

Overall, the process according to the invention, comprising the production of nitrobenzene by adiabatic nitration of benzene with subsequent two-stage performance of the evaporation for concentration of the spent acid, leads to higher plant availability, lower maintenance costs, lower investment costs and lower energy costs.

The above advantages of the process according to the invention are surprising in light of the prior art, as discussed above, because the prior art discloses either a single-stage evaporation or a multi-stage evaporation which relates, however, to material systems which do not exhibit the particular problems of nitrobenzenes.

In the present case of the mononitration of benzene, the concentration and boiling temperature difference required, as mentioned above, to enable the heat of condensation to be used, as described in the prior art, does not exist, so that this procedure cannot suitably be applied to the single-stage procedure already described in connection with nitrobenzene.

In the process according to the invention, the product mixture obtained in the nitration has a temperature of at least 110° C. Accordingly, the spent acid, which is obtained by separation of the crude nitrobenzene, likewise has approximately that temperature.

Preferably, the temperature of the product mixture obtained in the nitration, and accordingly the temperature of the spent acid, is at least 120° C.

Preferably, the temperature of the product mixture obtained in the nitration, and accordingly the temperature of the spent acid, is not more than 150° C.

Maintenance of the above-mentioned minimum temperature of 110° C., preferably 120° C., ensures that sufficient energy in the form of heat is present in the subsequent two-stage separation by evaporation in order to achieve an adequate separating efficiency of the water even at the less reduced pressures.

The spent acid is concentrated by separation by means of evaporation of in particular water in two stages.

According to the invention, the heat for the evaporation of water comes substantially from the reaction enthalpy of the preceding, adiabatic nitration.

In connection with the present invention, substantially means that a proportion of at least 90%, preferably 95%, of the heat for the evaporation comes from the adiabatic nitration reaction, the reaction product in itself containing sufficient enthalpy to achieve that value.

Particularly preferably, no further heat is supplied to the spent acid in the two stages of step i) of the process according to the invention. Accordingly, it follows that the evaporators are likewise operated adiabatically.

In an embodiment of the present process according to the invention that is likewise preferred, a proportion of up to 10% of the heat used for the evaporation is fed to the two stages from outside the process.

One or both evaporators can additionally be provided with heating steam or another external heat supply.

This embodiment is preferred because it allows the evaporation to be influenced in a regulating manner, which would otherwise be possible only via pressure adjustments, which are, however, slower to respond than an immediate temperature adjustment in the particular stage of the evaporation.

Accordingly, for its technical advantageousness in terms of the above-mentioned energy saving, the present process according to the invention is not dependent on the further supply of heat in the two stages of the evaporation, but uses that heat in a preferred manner solely for better control of the process as a whole in terms of process technology.

The feed of spent acid to the first stage according to i) contains preferably from 60 to 75% by mass, particularly preferably from 65 to 70% by mass, $H_2SO_4$.

As well as containing water and sulfuric acid, the spent acid can contain nitrobenzene, benzene and the secondary products of the benzene nitration (dinitrobenzene, nitrophenols and oxalic acid). Nitric acid and also dissolved nitrous gases can also be present.

The separated vapour of each stage according to i) is preferably liquefied by single- or multi-stage condensation and fed to a phase separator in order also to separate off condensed organic liquid.

In order that the concentrated sulfuric acid can expediently be fed back into the reaction, it should have, after passing through both stages of step a content by mass of $H_2SO_4$ of not less than 65%, preferably not less than 68%, particularly preferably from 69% to 72%.

The present invention further provides a plant for the production of nitrobenzene, comprising a reactor (1), a phase separator (2), two evaporator and condensation devices connected to vacuum installations (7, 9), and optionally a storage container (5), characterised in that the plant has a first evaporator (3) with an associated first condenser (8) and a connected vacuum installation (9) and a second evaporator (4) with an associated second condenser (6) and a connected vacuum installation (7), and wherein the first evaporator (3) is connected directly to the second evaporator (4) for the transfer of components that have not been evaporated, and wherein the heat exchange surface of the first condenser (8) is less than or equal to twice the heat exchange surface of the second condenser (6).

The plant according to the invention is particularly advantageous because, owing to the presence of the two above-mentioned evaporator and condensation devices connected to vacuum installations (7, 9) in immediate connection and owing to the ratio according to the invention of the heat exchange surfaces, it is ensured overall that the total heat exchange surface for the concentration of the above-mentioned spent acid achieved in the plant inter alia can be reduced.

As a result, the investment costs of such a plant are reduced significantly despite the provision of further—as compared with the prior art—plant parts in the form of the second evaporator, or the second condenser (6), and the second vacuum installation (7). This is accompanied by the possibility of using in such a plant according to the invention vacuum installations which are of smaller overall dimensions than an individual vacuum installation as used in the prior art. This reduces the investment costs of such a plant further. At the same time, the above-mentioned plant according to the invention is not only advantageous in respect of its investment costs as compared with the prior art but, in connection with the process according to the invention disclosed herein, also results in a reduction in the operating costs of the plant as compared with the prior art, but the recyclability of the sulfuric acid used in the process is not impaired as a result.

Conventionally, all parts of the plant that come into direct contact with liquid constituents of the substances treated in the plant are either enamelled on their inside walls or are made of tantalum or similar materials that are resistant to hot sulfuric and nitric acid.

In a further embodiment of the plant according to the invention, the vacuum installations (7, 9) are so arranged that the second vacuum installation (7), which is connected to the second condenser (6), feeds into the first condenser (8), the first vacuum installation (9) continuing to draw from the first condenser (8). As a result, the second vacuum installation (7) can be of smaller dimensions because it no longer feeds against the ambient pressure but against the pressure which has already been reduced by the first vacuum installation (9) according to the process of the invention to from 100 mbar to 300 mbar. This results in a further saving in energy and investment costs.

The process according to the invention is explained in greater detail hereinbelow by means of drawings and examples, without being limited thereto.

FIG. 1 shows in diagrammatic form a preferred embodiment of the process according to the invention, or of the plant according to the invention, in which a sulfuric acid stream (S3) and nitric acid (S2) and benzene (S1) are fed to a reactor (1).

When the nitric acid has reacted completely with benzene under adiabatic conditions in the reactor (1) to give nitrobenzene and water, the reaction mixture (S4) thereby heated to about 135° C. (see the examples) is fed to a phase separator in the form of a decanter (2), in which the reaction mixture is separated into a phase of crude nitrobenzene (S5) and spent acid (S6). The spent acid (S6) is partially concentrated in a first evaporator (3) operated at 260 mbar. Also shown is a false air stream (S16), which is drawn into the first evaporator (3) by the vacuum therein. The vapour stream (S12) produced in the first evaporator (3), comprising water, sulfuric acid, nitrobenzene, benzene and aliphatic organic compounds, which are contained as impurities in the benzene stream (S1) for reaction, are condensed in a condenser (8) to a first liquid discharge stream (S13). The unevaporated, liquid discharge stream of the first evaporator (S7) is fed to the second evaporator (4), which is operated at a pressure of 74 mbar, and thereby concentrated to a concentration of 70% by mass sulfuric acid (S8). Also shown is a second false air stream (S15), which is drawn into the second evaporator (3) by the vacuum therein. For further use, the re-concentrated sulfuric acid (S8) is accordingly stored in a sulfuric acid tank (5). In the second evaporation of the spent acid there is obtained a vapour stream (S9) consisting substantially of water as well as residues of sulfuric acid, nitrobenzene and benzene, which is condensed in a condenser (6).

A large portion of the non-condensable gases dissolved in the spent acid (S6) passes in the first evaporator (3) into the vapour phase (S12) and is discharged as non-condensable vapour phase (S14) via the vacuum installation (9) of the first condenser (8). The majority of the organic components dissolved in the spent acid, which boil more easily than water, likewise pass in the first evaporator (3) into the vapour phase (S12) and are condensed in the condenser (8) to stream (S13). In the second evaporator (4), the vapour phase (S9) consists substantially of water and nitrobenzene, so that the saturation temperature in the condenser (6) is determined by the component water, which can be discharged from the process as liquid stream (S10). Remaining non-condensable gases (S11) are discharged via the vacuum installation of the second condenser (7).

The saturation temperature of the vapour phase (S9) is higher at comparable pressure than that of the vapour phase (S12) which would result from a single-stage concentration of the sulfuric acid.

Figure 2:
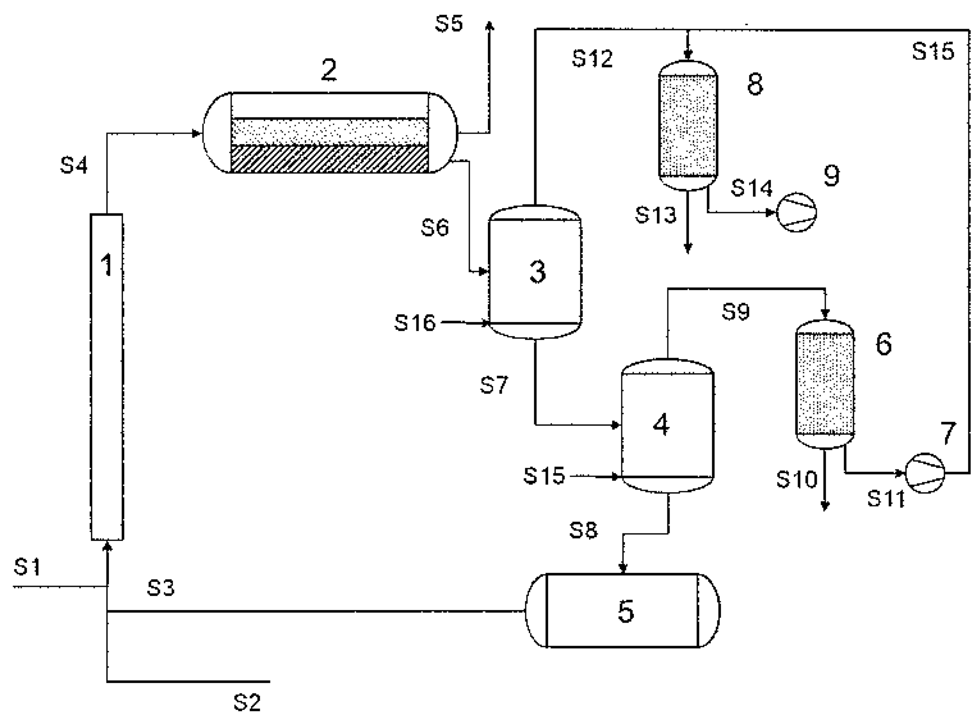
FIG. 2 shows a further, particularly preferred embodiment of the process according to the invention, or of the plant according to the invention, which is substantially identical with that according to FIG. 1 but differs in that the gas stream (S15) is guided from the second vacuum installation (7) into the first condenser (8), so that the gas stream (S15) and the vapour phase (S12) from the first evaporator (3) are guided together into the first condenser (8).

FIG. 2 shows a further, particularly preferred embodiment of the process according to the invention, or of the plant according to the invention, which is substantially identical with that according to FIG. 1 but differs in that the gas stream (S15) is guided from the second vacuum installation (7) into the first condenser (8), so that the gas stream (S15) and the vapour phase (S12) from the first evaporator (3) are guided together into the first condenser (8). This results in a second vacuum installation (7) of smaller dimensions.

EXAMPLES

Example 1 (Comparison Example)

Single-Stage Evaporation

The concentration of the dilute sulfuric acid by single-stage evaporation was simulated by means of a process model. The process parameters and mass flows for this simulation calculation were taken from the example in US 2001 0043894 A1.

This procedure corresponds to that of FIG. 1, with the difference that the devices (3), (8) and (9) do not exist and the stream (S6) accordingly passes directly into the evaporator (4). That is to say, the evaporation takes place in a single stage according to the prior art.

A mixture consisting of an acid stream with contents by mass of 65.7% $H_2SO_4$, 4.0% $HNO_3$ and 30.3% $H_2O$ and a benzene stream are fed to the reactor (1). The benzene is used in an amount such that a molar ratio of 1.1:1 of benzene to $HNO_3$ is established.

The total volume flow through the reactor (1) is 173 $m^3$/h.

The stream (S4) leaves the reactor (1) with an adiabatic reaction procedure at 135° C. and is fed to a phase separator (decanter, 2). With a phase ratio between benzene and acid stream of 1:18.5 according to parts by weight at the entry to the reactor (1), the stream (S4) separates in the phase separator (2) into a spent acid phase (S6) with 157 $m^3$/h and a crude nitrobenzene phase (S5) with 16 $m^3$/h.

The temperature of the spent acid (S6), which leaves the phase separator (2) as the heavy phase, is 135° C. and the sulfuric acid content is 67.2% by mass.

In order to achieve a concentration of the sulfuric acid to 70% by mass stream (S8), the temperature in the evaporator (4) is 95° C. and the pressure is 74 mbar.

The vapour stream (S9) formed in an amount of 9.3 t/h consists substantially of steam, which is fed to a condenser (6).

Taking into consideration a pressure loss of 10 mbar between the evaporator (4) and the condenser (6), a condensation pressure of 64 mbar is accordingly obtained.

Under these conditions, the vapour phase (S9) can be condensed to a content of 0.6% at a cooling water supply temperature of 30° C. and a temperature difference of 2 K between the cooling water side and the process side.

To that end, 5.56 MW of heat of condensation must be dissipated. A condenser with a heat transfer surface of 920 $m^2$ is required for that purpose.

The non-condensable portion is discharged as waste gas stream (S11) via the vacuum installation (7).

The corresponding volume flow is 850 $m^3$/h. The required power of a suitable vacuum installation (7) for feeding that volume flow of 850 $m^3$/h at 64 mbar suction pressure is about 40 kW.

For the entire vacuum system of a single-stage evaporation, a false air stream (S15) of 10 kg/h is assumed on the basis of operational empirical values, which stream passes from outside into the system part operated under vacuum via minimal leaks in flange connections.

Example 2 (According to the Invention)

Two-Stage Evaporation

This process alternative corresponds to FIG. 1. The temperature of the spent acid (S6), which leaves the phase separator (2) as the heavy phase, is again 135° C. and the sulfuric acid content is 67.1% by mass.

The spent acid (S6) is first led to the first evaporator (3). In the first evaporator (3), the spent acid is concentrated to 68.2% by mass, a pressure of 260 mbar and a temperature of 120° C. being established in the evaporator (3).

The resulting vapour phase (S12) is fed to the condenser (8). Taking into consideration a pressure loss, analogous to Example 1, of 10 mbar between the evaporator (3) and the condenser (8), a condensation pressure of 250 mbar is accordingly obtained.

Under these conditions, the vapour phase (S12) can be condensed to a content of 0.39% at a cooling water supply temperature of 30° C. and a temperature difference of 2 K between the cooling water side and the process side. To that end, 1.92 MW of heat of condensation are dissipated. A condenser (8) with a heat transfer surface of 82 $m^2$ is required for that purpose.

The non-condensable portion is discharged as waste gas stream (S14) via the vacuum installation (9). The corresponding volume flow is 4.5 $m^3$/h. The required power of a suitable vacuum installation (9) for feeding a suction stream of 4.5 $m^3$/h at 250 mbar suction pressure is about 1 kW.

The liquid discharge (S7) from the first evaporator is fed to a second evaporator (4). In order to achieve a concentration of the sulfuric acid to 70% by mass in the stream (S8), a temperature of 95° C. and a pressure of 74 mbar are established in the second evaporator (4).

The resulting vapour phase (S9) is fed to a further condenser (6). Taking into consideration a pressure loss of 10 mbar between the evaporator (4) and the condenser (6), a condensation pressure of 64 mbar is accordingly obtained.

Under these conditions, at a cooling water supply temperature of 30° C. and a temperature difference of 2 K between the cooling water side and the process side, the vapour phase (S9) can be condensed to a content of 0.54%.

To that end, 3.64 MW of heat of condensation must be dissipated. A condenser (6) with a heat transfer surface of 640 $m^2$ is required for that purpose.

The non-condensable portion is discharged as waste gas stream (S11) via the vacuum pump (7). The corresponding volume flow is 405 $m^3$/h. The required power of a suitable vacuum installation for feeding a suction stream of 405 $m^3$/h at 64 mbar suction pressure is about 25 kW.

The ratio of the mass flows of vapour phase (S12) from the first evaporator (3) mid vapour phase (S9) from the second evaporator (4) is 1:1.6 in this example.

Compared with the process according to the prior art (Example 1), the required heat transfer surface for condensation of the vapour streams can accordingly be reduced by 22% from 920 $m^2$ to 722 $m^2$ using a two-stage evaporation.

In addition, the required total power of the vacuum installations falls by 35% from 40 kW to 26 kW.

For the overall vacuum system comprising the two vacuum installations (e.g. two compressors or vacuum pumps) of a two-stage evaporation, a leakage rate (so-called "false air stream") (S15, S16) of 10 kg/h per evaporator, that is to say 20 kg/h in total, was assumed on the basis of operational empirical values, which passes from outside into the plant part operated under vacuum via minimal leakages in flange connections.

That is to say, the process according to the invention is still advantageous over processes from the prior art even in the case of larger "false air streams".

Example 3 (According to the Invention)

Two-Stage Evaporation

This process alternative corresponds to FIG. 1. The temperature of the spent acid (S6), which leaves the phase separator (2) as the heavy phase, is again 135° C. and the sulfuric acid content is 67.1% by mass.

The spent acid (S6) is first fed to the first evaporator (3). In the first evaporator (3), the spent acid is concentrated to 69.0% by mass, a pressure of 135 mbar and a temperature of 106° C. being established in the evaporator (3).

The resulting vapour phase (S12) is fed to the condenser (8). Taking into consideration a pressure loss, analogous to Example 1, of 10 mbar between the evaporator (3) and the condenser (8), a condensation pressure of 125 mbar is accordingly obtained. Under these conditions, the vapour phase (S12) can be condensed to a content of 0.30% at a cooling water supply temperature of 30° C. and a temperature difference of 2 K between the cooling water side and the process side. To that end, 3.56 MW of heat of condensation are dissipated. A condenser (8) with a heat transfer surface of 350 $m^2$ is required for that purpose.

The non-condensable portion must be discharged as waste gas stream (S14) to the vacuum pump (9). The corresponding volume flow is 140 $m^3$/h. The required power of a suitable vacuum pump for feeding a suction stream of 140 $m^3$/h at 125 mbar suction pressure is 6 kW.

The liquid discharge (S7) from the first evaporator is fed to a second evaporator (4). In order to achieve a concentration of the sulfuric acid to 70% by mass in the stream (S8), the temperature in the second evaporator (4) must be 95° C. and the pressure 74 mbar.

The resulting vapour phase (S9) is fed to the condenser (6). Taking into consideration a pressure loss of 10 mbar between the evaporator (4) and the condenser (6), a condensation pressure of 64 mbar is accordingly obtained. Under these conditions, at a cooling water supply temperature of 30° C. and a temperature difference of 2 K between the cooling water side and the process side, the vapour phase (S9) can be condensed to a content of 1%. To that end, 1.98 MW of heat of condensation must be dissipated. A condenser (6) with a heat transfer surface of 320 $m^2$ is required for that purpose. The non-condensable portion must be discharged as waste gas stream (S11) to the vacuum pump (7). The corresponding volume flow is 430 $m^3$/h. The required power of a suitable vacuum pump for feeding a suction stream of 430 $m^3$/h at 64 mbar suction pressure is about 27 kW. The ratio of the mass flows of vapour phase (S12) from the first evaporator and vapour phase (S9) from the second evaporator is 2:1 in this example.

Compared with Example 1, the required heat transfer surface for condensation of the vapour streams can accordingly be reduced by 28% from 920 $m^2$ to 670 $m^2$ using a two-stage evaporation. In addition, the required power of the vacuum pumps falls by 18% from 40 kW to 33 kW. For the overall vacuum system of a two-stage evaporation, a false air stream (S15) of 10 kg/h per evaporator, that is to say 20 kg/h in total, was assumed on the basis of operational empirical values, which passes from outside into the plant part operated under vacuum via minimal leakages in flange connections.

Compared with Example 2, the required heat transfer surface for condensation of the vapour streams is in Example 3 reduced, by 52 $m^2$ to a value of 670 $m^2$, whereas the the required power of the vacuum pumps is increased by 7 kW to a value of 33 kW. Whether an embodiment of the inventive process according to Example 2 or Example 3 is to be preferred depends on the boundary conditions (for example, development of energy prices).

The invention claimed is:

1. A process for the production of nitrobenzene by means of adiabatic nitration of benzene with nitric acid in the presence of sulfuric acid, in which a) the product mixture obtained in the nitration is separated into spent acid and crude nitrobenzene and b) at least the water contained in the spent acid is partially separated from the sulfuric acid contained therein and c) the sulfuric acid so concentrated is fed to the nitration again, which process is characterised in that i) the separation according to step b) is carried out by evaporation in two stages with an absolute pressure that falls from the first stage to the second stage from 100 mbar to 300 mbar to 50 mbar to 150 mbar;

ii) a proportion of at least 90% of the heat for the evaporation comes from the reaction enthalpy of the adiabatic nitration reaction and iii) the product mixture obtained in the nitration has a temperature of at least 110° C.

2. The process according to claim 1, characterised in that the product mixture obtained in the nitration has a temperature of at least 120° C.

3. The process according to claim 1, characterised in that the heat for the evaporation according to step ii) comes solely from the reaction enthalpy of the adiabatic nitration reaction.

4. The process according to any one of the preceding claims, characterised in that the feed of spent acid to the first stage according to i) contains from 60 to 75% by mass $H_2SO_4$.

5. The process according to claim 1, 2 or 3, characterised in that the steam separated in each stage according to i) is liquefied by condensation.

6. The process according to claim 5, characterised in that the liquefied steam separated off is fed to a phase separator.

7. The process according to claim 1, 2 or 3, characterised in that the concentrated sulfuric acid according to step c), after passing through both stages of step i), has a content by mass of $H_2SO_4$ of not less than 65%.

* * * * *